United States Patent [19]

Woodruff

[11] Patent Number: 4,995,555

[45] Date of Patent: Feb. 26, 1991

[54] AIR TREATMENT DEVICE AND METHOD

[75] Inventor: Keith F. Woodruff, Mountainside, N.J.

[73] Assignee: American Cyanamid Company, Stamford, Conn.

[21] Appl. No.: 270,575

[22] Filed: Nov. 14, 1988

[51] Int. Cl.$^5$ .............................................. A61L 9/04
[52] U.S. Cl. ........................................ 239/43; 239/37; 239/55; 239/58
[58] Field of Search ............... 239/34, 54, 56, 37, 239/43, 53, 55, 58, 59; 141/310, 330; 206/0.5

[56] References Cited

U.S. PATENT DOCUMENTS

| | | | |
|---|---|---|---|
| 732,203 | 6/1903 | Lowry | 141/330 |
| 1,341,525 | 11/1920 | Vericel | 239/43 |
| 2,657,090 | 10/1953 | Meek | 239/55 |
| 3,727,840 | 4/1973 | Nigro | 239/43 |
| 4,161,284 | 7/1979 | Rattan | 239/43 |
| 4,247,042 | 1/1981 | Schimanski et al. | 239/59 |
| 4,505,429 | 3/1985 | Mandon | 239/56 |
| 4,526,320 | 7/1985 | von Philipp et al. | 239/34 |
| 4,549,693 | 10/1985 | Barlics | 239/55 |
| 4,630,775 | 12/1986 | Mandon et al. | 239/56 |

FOREIGN PATENT DOCUMENTS 2014854  9/1979  United Kingdom ............... 239/56

Primary Examiner—Andres Kashnikow
Assistant Examiner—Christopher G. Trainor
Attorney, Agent, or Firm—Anthony M. Santini

[57] ABSTRACT

An air treating device including a liquid reservoir having a mouth opening, a base supporting and surrounding a liquid absorbent material, a piercing pin extending upwardly from the base and absorbent material, a mechanism for attaching the reservoir to the base such that the pin is in direct alignment with the mouth opening, and a liquid metering control mechanism surrounding the pin and between the mouth opening and the absorbent material, whereby the device provides a rate of dispersion which is substantially even over an extended period of time.

21 Claims, 6 Drawing Sheets

AIR TREATMENT DEVICE AND METHOD

BACKGROUND OF THE INVENTION

The present invention relates generally to a vapor dispersing device and process utilizing a volatile fluid for treating air and the like and, more particularly, to a gravity fed liquid system in which the rate of dispersion is substantially even over an extended period of time.

Deodorizers, fumigators, purifiers, and other vaporizer-type air treatment devices using a volatile fluid are well known in the art to produce vapors in particular ways to remove odors, discourage pests, etc. Some of these devices rely on solid or solid-like treatment agents which sublime or evaporate upon exposure to air. Other treatment devices utilize vaporization of liquid either directly through sprays, drip dispensers or the like, or indirectly through wicks or saturated pads, to provide air treating vapors.

There are two known types of gravity fed liquid evaporators. Typically, in one type, the gravity fed system is comprised of an inverted bottle supported within a cup or pan holding a pool of liquid at the bottom thereof. The mouth of the bottle is positioned a short distance above the bottom of the cup or pan such that volatile liquid from the bottle flows into the cup until the level reaches the mouth of the bottle, where the flow is stopped by atmospheric pressure. As soon as the liquid level falls below the mouth of the bottle, due to evaporation taking place from the surface of this pool, flow from the bottle starts again and, as a result, the liquid level is maintained at the level of the mouth of the bottle. However, if one of these devices is knocked over, or its parts are displaced, the contents of the pool are spilled and the liquid is lost from the bottle. Not only may mess and waste occur, but the increased concentration of vapors may be troublesome and the liquid itself may be one that should be confined. The following list of U. S. Patents discloses a representative sample of such prior art inverted liquid systems:

| | |
|---|---|
| 436,130 | to Gubelman |
| 1,099,720 | to Peck |
| 2,481,296 | to Dupuy |
| 2,586,179 | to Rooch |

In gravity fed systems of the other type, various provisions have been made for preventing the evaporation of the liquid until it is desired to actuate the dispenser. These provisions have included using a screw threaded neck for the bottle and a removable cap, or a closure having screw threads, as in U.S. Pat. Nos. 1,755,901, 1,818,648, 1,974,414, 2,166,969 and 2,586,179. However, dispensers having screw threaded bottle necks have added undesirably to the complexity and manufacturing cost thereof and also have limited usefulness.

In inverted bottle evaporators of a similar type, the user must make a fine puncture of the closure end of the bottle to provide a seepage opening, the outcome of which may be an improper rate of evaporation if the opening is made too small or too large, or if the parts are not in proper relation to each other. Unfortunately, none of the devices embodied in the prior art possesses a design which contributes to a performance which is likely to make them much more effective than a device which functions on a principle as basic as an unattended open bottle. Thus, there remains a need and a demand in the art for further improvements in gravity fed liquid system air treatment devices.

There have been numerous methods devised which attempt to regulate the diffusion rate of volatile materials, especially with regard to the fragrancing and deodorization of an enclosed room. The primary function of these types of devices for commercial use has been in the area of deodorization and counteractancy of malodors. However, as the focus begins to change from dispensing of fragrance compounds, which are meant to mask malodors, to the controlled release of fine fragrances, solely for the aesthetic appeal that these materials generate, it is clear that the prior art devices are not well suited to this function.

Although it is reasonable to imagine that it is within the scope of the present art to devise an apparatus which is capable of exerting some measure of control over the diffusion rate of a volatile material, the current devices, whether they are of the continuous element type of wicking mechanism (U.S. Pat. No. 4,537,351 to Wilson) or a device which uses a wick integral with an absorbent element (U.S. Pat. No. 4,413,779 to Santini) in fact offer little governance over the rate at which diffusion takes place. The most volatile and fugitive components of the fragrance, which are often those most easily perceived olfactively, are prematurely lost and, as a result, are not available for dispensing throughout the life of the device. However, according to the present invention, there is disclosed a device which represents an advance over what is currently known in this area, while providing a dispenser characterized by the simplicity of the structure thereof.

SUMMARY OF THE INVENTION

It is therefore an object of the present invention to provide an improved and simplified gravity fed air treatment device which does not suffer from the aforementioned drawbacks of the prior art devices.

It is another object of the present invention to provide a continuous gravity fed air treatment device with a liquid metering control.

It is a further object of the present invention to provide an improved air treatment device that enables fragrance to be released in a definite, predetermined, uniform manner.

It is a still further object of the present invention to provide such an improved air treatment device in which the emitted fragrance level is adjustable.

Related to all of the foregoing objects, it is an aim of the present invention to provide a new and improved air treatment device that is significantly effective while being very simple in construction, economical to manufacture, and which is absolutely closed until it is put in operation.

In accordance with one embodiment of the present invention, there is provided an air treatment device as a two-piece molded construction utilizing the minimum amount of materials and parts necessary to manufacture an effective, reliable apparatus. In its preferred, embodiment, the device is molded of high grade polyethylene or polypropylene, or other thermoplastic or thermoset resin.

The device is provided with a liquid reservoir mounted upon a base. The reservoir has a mouth opening which, before activation, is closed by a membrane seal. The seal can be a thin foil or any other easily pierceable material.

A plurality of longitudinal slots are provided around the circumference of the reservoir and render the device adjustable, so that its evaporating capacity may be regulated in accordance with the size of the room to be deodorized and the nature of the odor to be destroyed. Also circumferentially positioned about the reservoir are one or more lateral beads. The beads serve to provide a snap attachment of the reservoir onto the base. Lastly, the reservoir includes a plurality of aperture limiting means which operate in co-relation to the longitudinal slots to provide the aforementioned evaporation regulation ability.

The base has a plurality of sidewall segments with apertures therebetween. Connectors link adjoining sidewall segments to each other to provide vertical support and minimize outward sidewall deflection when the reservoir is engaged with the base. A plurality of support means are positioned in the lower half of the area defined by said sidewall segments for vertically supporting the reservoir when the air treatment device is in operation. The top half of the area defined by the sidewall segments consists of upper and lower circumferential grooves, which correspondingly mate with the lateral beads to provide the aforementioned snap attachment. A pin is positioned in the center of the base and in direct alignment with the mouth opening of the reservoir. An air-liquid control interface, a thin, mesh-like material, surrounds the pin and is positioned directly atop absorbent material.

Before activation, the mouth opening rests just slightly above the pin so that the seal is not punctured thereby. When it is desired to operate the device, the reservoir is pressed down into the base such that the lowest lateral bead snaps into engagement with the lower circumferential groove. The downward pressure also causes the pin to concurrently puncture the membrane seal, thereby allowing for relatively unimpeded gravity flow of liquid between the reservoir and absorbent material and, furthermore, positioning the air-liquid control interface between the mouth opening and the absorbent material. Such flow continues until the absorbent material becomes saturated with the liquid.

Once saturated, the absorbent material swells against the control interface creating an hydraulic seal between the reservoir and the absorbent material. Air is thereby prevented from entering the reservoir, thus stopping further flow of the liquid until the liquid in the absorbent material is vaporized. As the evaporation proceeds, air is permitted to re-enter the reservoir and resume fluid flow. The absorbent material then takes up more of the liquid, thereby rendering the operation continuous and maintaining a uniform release of fragrance to the environment.

While in the activated state, the level of fragrance emitted by the device may be adjusted by relative rotation of the reservoir with respect to the base. Although the reservoir is snapped onto the base, they nonetheless remain in rotational engagement with each other. When the slots are in alignment with the sidewall segments, the open area of the aperture is in alignment with the aperture limiting means of the reservoir. Thus, the open area for evaporation of the volatile composition from the absorbent material is minimized.

However, when the slots are brought into alignment with the apertures, by rotation of the reservoir, the maximum open area for evaporation is created via the apertures, thereby allowing the vaporizing fragrance to escape more quickly. Accordingly, for larger rooms or obnoxious odors, it may be desired to align the slots with the apertures. However, for smaller rooms and less malodorous scents, the evaporation capacity of the device may be regulated by rotating the aperture limiting means into alignment with the apertures. In this manner, the continuously operating device is rendered adjustable.

DETAILED DESCRIPTION OF THE INVENTION

Figure 1:
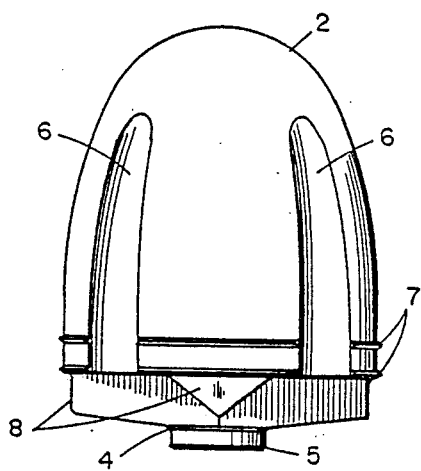
FIG. 1 is a side view of the liquid reservoir of the air treatment device of the present invention.
Figure 2:
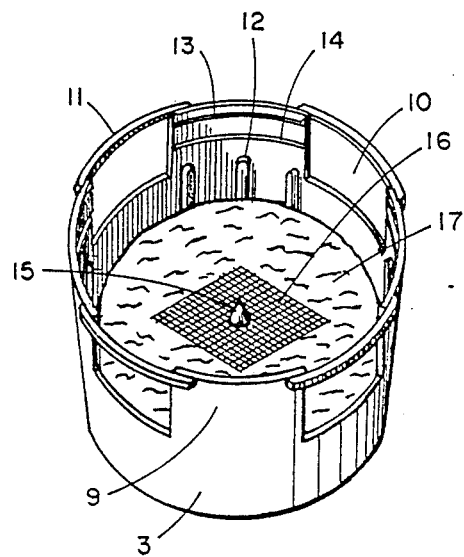
FIG. 2 is a perspective view of the base of the air treatment device.
Figure 5:
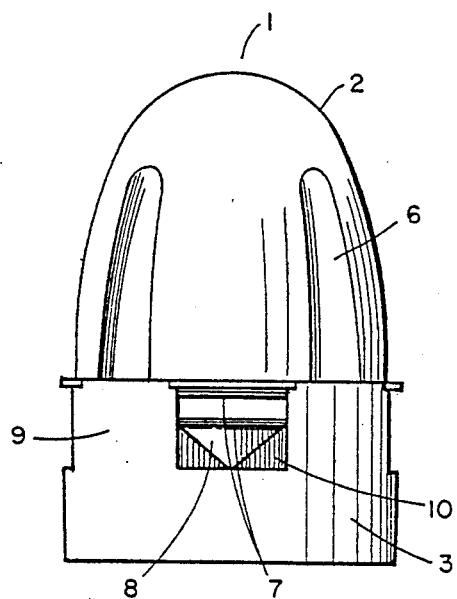
FIG. 5 is a side view of the air treatment device embodying the present invention.

As specifically embodied herein and depicted in FIGS. 1, 2 and 5, a two-piece air treatment device 1 is provided having liquid reservoir 2 mounted upon base 3. Reservoir 2 includes mouth opening 4 which, before activation, is closed by membrane seal 5. The seal can be a thin foil or any other easy pierceable material.

A plurality of fully longitudinal slots 6 are provided around the circumference of reservoir 2. As will be explained in more detail later, slots 6 render the device adjustable, so that its evaporating capacity may be regulated in accordance with the size of the room to be deodorized and the nature of the odor to be destroyed. Also circumferentially positioned about reservoir 2 are one or more lateral beads 7. As will also be more fully explained herein, beads 7 serve to provide a snap attachment of reservoir 2 onto base 3. However, attachment can also be provided by, for example, threaded rotation of reservoir 2 onto base 3. Lastly, liquid reservoir 2 includes a plurality of aperture limiting means 8 which operate in co-relation to longitudinal slots 6 to provide the aforementioned evaporation regulation ability.

Base 3 has a plurality of sidewall segments 9 with apertures 10 therebetween. Connectors 11 link adjoining sidewall segments to each other to provide vertical support and minimize outward sidewall deflection when reservoir 2 is engaged with base 3. A plurality of support means 12 are positioned in the lower half of the area defined by said sidewall segments 12 for vertically supporting reservoir 2 when air treatment device 1 is in operation. The top half of the area defined by sidewall segment 9 consists of upper circumferential groove 13 and lower circumferential groove 14, for correspondingly receiving lateral beads 7 of reservoir 2. Pin 15 is positioned in the center of base 3 and in direct alignment with opening 4 of reservoir 2. Air-liquid control interface 16, a thin, mesh-like material, surrounds pin 15 and is positioned directly atop absorbent material 17 to provide a liquid metering control.

Figure 3:
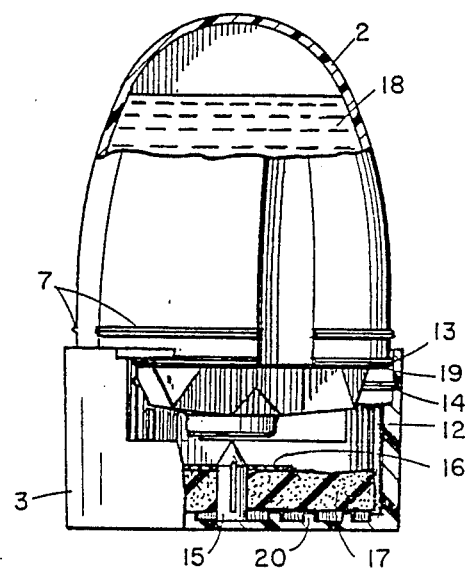
FIG. 3 is a cross-sectional view of the device of the present invention in the position before activation.
Figure 4:
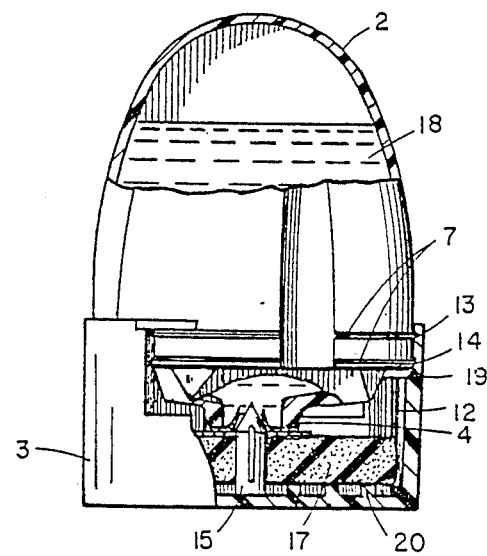
FIG. 4 is a cross-sectional view of the device of the present invention in the position during operation.

With reference to FIGS. 3 and 4, the related functions of the foregoing will be more easily understood. FIG. 3 shows the two-piece air treatment device in position before activation. Reservoir 2 and base 3 are designed such that, when the lowest lateral bead 7 falls into snapped engagement with upper circumferential groove 13, mouth opening 4 rests just slightly above pin 15 so that seal 5 is not punctured thereby.

When it is desired to operate the device, as shown in FIG. 4, reservoir 2 is pressed down into base 3 and the lowest lateral bead 7 snaps into engagement with lower circumferential groove 14. If more than one lateral bead is provided, the reservoir will be designed such that it will, at this time, correspondingly mate with upper circumferential groove 13. As beads 7 are pressed into grooves 13 and/or 14, the downward pressure causes pin 15 to concurrently puncture membrane seal 5, thereby allowing for relatively unimpeded flow of liquid between reservoir 2 and absorbent material 17 and, furthermore, positioning air-liquid control interface 16 between mouth opening 4 and absorbent material 17. Such flow continues until absorbent material 17 becomes saturated with the liquid.

Absorbent pad 17 is made of any cellulosic fabric, felt, porous plastic or any other porous structure having sufficient void volume. Once saturated, absorbent material 17 swells against control interface 16, creating an hydraulic seal between reservoir 2 and the top surface of saturated absorbent material 17. Air is thereby prevented from entering the reservoir, thus stopping further flow of the liquid until the liquid in the absorbent material is vaporized. That is to say, after the liquid evaporates from absorbent material 17 and diffuses into the environment, commingling with the ambient air in the room, air is permitted into reservoir 2, resuming fluid flow. Absorption of the liquid by absorbent material 17 and subsequent drying of the latter due to vaporization cause the level of liquid in reservoir 2 to drop.

It is to be understood, therefore, that when the absorbent material has become saturated with the liquid, the flow of the liquid thereafter will depend upon the vaporization taking place from the surface of the absorbent material. As the evaporation proceeds, the absorbent material takes up more of the liquid, thereby rendering the operation continuous and maintaining a uniform release of fragrance to the environment.

To this end, the bottom of base 3 is provided with a plurality of spacers 20, upon which absorbent material 17 rests. The combination of spacers 20 and support means 12 serve to provide the maximum exposed surface area of absorbent material 17. By allowing air to surround saturated absorbent material 17, maximum vaporization can be effected.

As one can see, the thickness and mesh design of control interface 16 must be selected based upon the critical flow characteristics of the particular volatile liquid so that the liquid flow metering out from the reservoir is appropriately controlled.

It should be understood that control interface 16 creates a true air-liquid management system. If control interface 16 was not present to regulate the air intake/liquid flow relationship, and absorbent material 17 became saturated with the volatile composition and swelled into direct contact with mouth opening 4, the subsequent evaporation of the volatile composition from absorbent material 17 would result in the absorbent material remaining permanently sealed against the portion of direct contact with the mouth opening, thereby rendering the air treatment device useless thereafter. Accordingly, control interface 16 is important for maintaining the continuous operation of the system, as well as providing a liquid metering control. Thus, the utility of control interface 16 is clearly evident.

The downward movement of mouth opening 4 upon control interface 16 is further regulated by the design dimensions of support means 12. As shown in FIG. 5, when the air treatment device is in the activated position, bottom lip 19 of reservoir 2 rests atop support means 12 so that no further downward movement of reservoir 2 into base 3 is possible. Accordingly, the combination of these features help to maintain the important design dimensions necessary to supply a sufficient quantity of the volatile liquid to keep the absorbent material 17 thoroughly and evenly saturated, while preserving the strength of the liquid until wholly exhausted.

While in the activated state, the level of fragrance emitted by the device may be adjusted by relative rotation of reservoir 2 with respect to base 3. As seen by reference to FIGS. 4 and 5, even though bead(s) 7 are snapped into grooves 13 and/or 14 to lock reservoir 2 onto base 3, they nonetheless remain in rotational engagement therewith.

When slots 6 are in alignment with sidewall segments 9, the open area of aperture 10 is in alignment with aperture limiting means 8 of reservoir 2. Thus, the open area for evaporation of the volatile composition from absorbent material 17 is minimized.

However, when slots 6 are brought into alignment with apertures 10 by rotation of reservoir 2, the maximum open area for evaporation is created via apertures 10, thereby allowing the vaporizing fragrance to escape more quickly. Accordingly, for larger rooms or obnoxious odors, it may be desired to align slots 6 with apertures 10. However, for smaller rooms and less malodorous scents, the evaporating capacity of the device may be regulated by rotating aperture limiting means 8 into alignment with apertures 10. In this manner, the continuously operating device is rendered adjustable.

Figure 11:
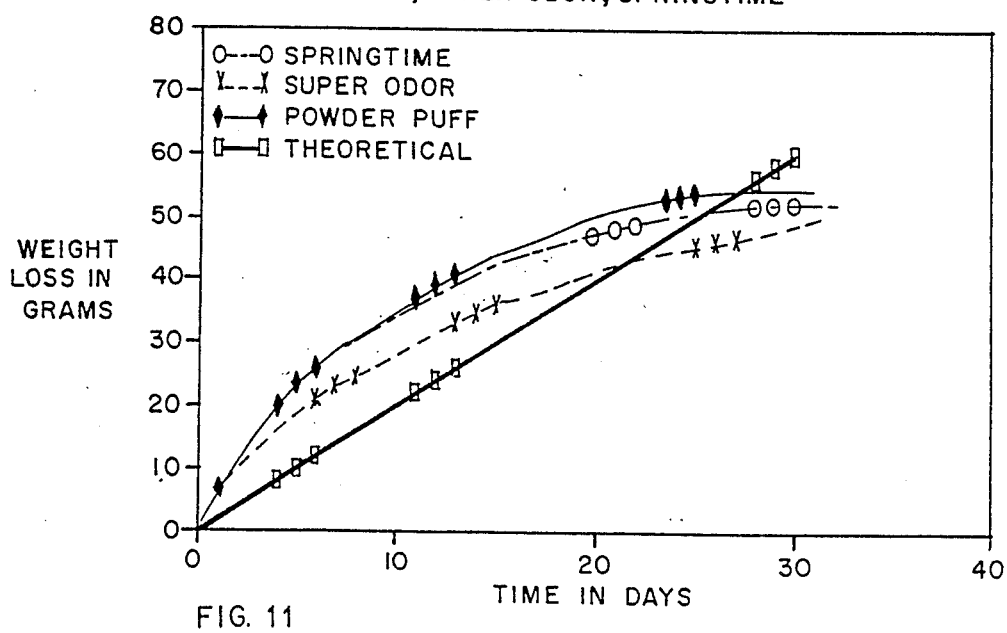
Figure 12:
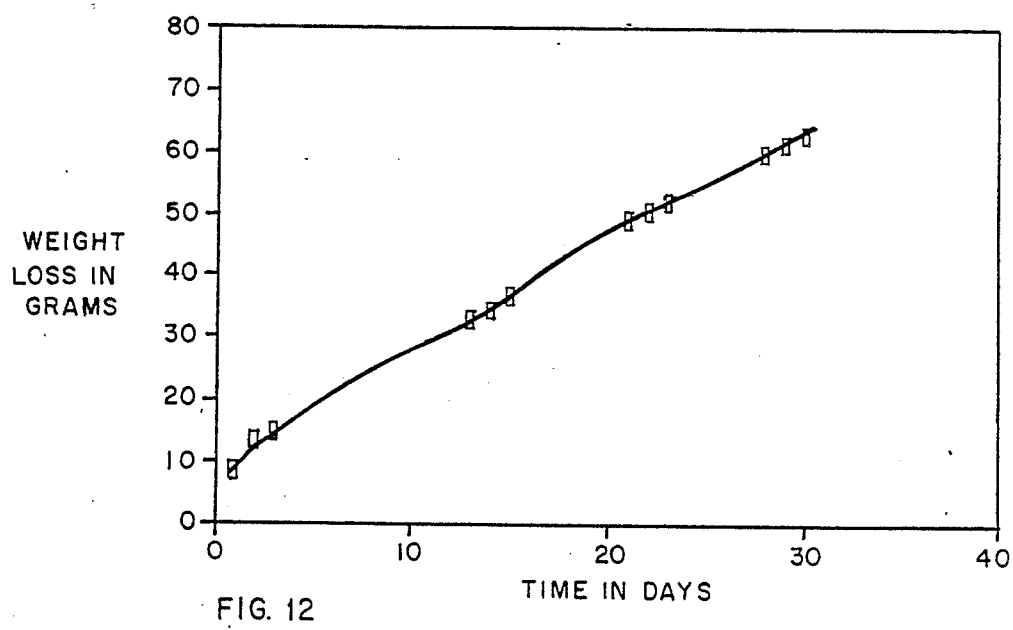
FIG. 12 is a graph plotting the dispersion rate of the present invention with a control interface.

To support the assertion herein that the present invention provides a continuous level of air treating material without premature loss of the most volatile and fugitive components of the fragrance, a comparison was conducted between the present invention with the control interface and Magic Mushroom ®, one of the market leaders in this commercial product area. Magic Mushroom ® is virtually identical in design and operation to that set forth in U.S. Pat. No. 4,413,779 (previously disclosed herein). FIGS. 11 and 12 plot the level of diffusion (weight loss in grams) of various Magic Mushroom ® scents with respect to useful life (time in days).

As is evident in FIGS. 11 and 12, the Magic Mushroom ® device starts off strong but, by the end of the third week, begins to level off. The Magic Mushroom ® diffusion curves are also plotted against the theoretical uniform dispersion curve.

However, as is shown in FIG. 12, the present invention with the control interface provides a truly uniform level of diffusion for a continuous month. These comparisons clearly evidence the superiority of one embodiment of the present invention.

An alternative embodiment of the present invention is disclosed in FIGS. 6A, 6B, 7 and 8. The embodiment therein is essentially identical to that disclosed in the first embodiment in this application, with the exception of the absence of a control interface. It has been surprisingly discovered by the inventors herein that results similar to those disclosed in the first embodiment can be obtained with the alternative embodiment disclosed in FIG. 6A by maintaining certain critical design parameters.

Figure 6A:
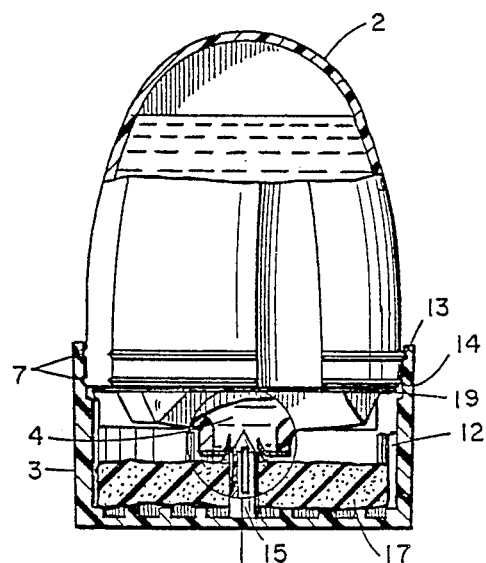
FIG. 6A is a cross-sectional view of an alternative embodiment of the present invention.
Figure 6B:
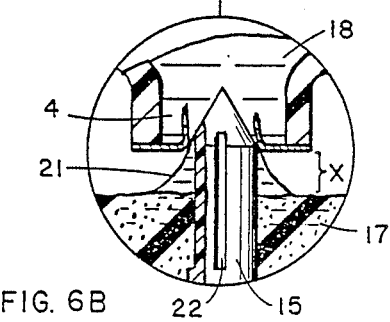
FIG. 6B is an exploded cross-sectional view of the area denoted in FIG. 6A.

Specifically, with reference to FIG. 6B, when an ebb height X of not greater than 1/16 of an inch is maintained in combination with particularly proportioned pin characteristics, an automatic air-liquid management system can be achieved. The ebb height X is more specifically described as the distance between the bottom of mouth opening 4 and the top surface of saturated absorbent material 17.

As previously mentioned, X is preferably no greater than 1/16 of an inch. This distance can be maintained by specifically designing base 3 so that the interaction of beads 7 with grooves 13 and/or 14, in combination with lower lip 19 resting upon support means 12, positions the bottom of mouth opening 4 within the required effective ebb height when absorbent material 17 is saturated.

When air treatment device 1 is placed into operation as hereinbefore explained, and the foregoing ebb height limitation is observed, it has been discovered that, after pin 15 pierces into mouth opening 4, liquid 18 flows out from mouth opening 4 directly onto absorbent material 17. Once absorbent material 17 is fully saturated via capillary action, it swells to bring the top surface thereof within the required effective ebb height. Once the effective ebb height X is achieved, ebb 21 forms along pin 15 between the bottom of mouth opening 4 and the top surface of saturated absorbent material 17. An hydraulic seal is formed as the surface tension of ebb 21 blocks air flow into the reservoir, and arrests any further escape of liquid 18 from reservoir 2.

As the liquid evaporates from absorbent material 17 and commingles with the air of the room, the ebb height will drop outside of the effective distance because ebb 21 will fade and air will enter mouth opening 4, allowing liquid 18 to escape therefrom until it again saturates absorbent material 17 to form ebb 21. At this point, the further escape of liquid 18 is again arrested. Thus, an automatic air-liquid management system is created.

Furthermore, ebb 21 performs the foregoing fluid flow cessation without the creation of a pool of liquid atop absorbent material 17. Accordingly, a gravity fed device is obtained which does not have the disadvantages associated with those pool-creating devices subject to spillage due to movement.

As previously alluded to, it has been discovered that particular design characteristics of pin 15 can effect a rate of dispersion of the volatile material which is substantially even over an extended period of time. With reference to FIGS. 6B through 8, there is shown a plurality of pin grooves 22 around the periphery of pin 15. Pin grooves 22 facilitate the flow of liquid 18 out of mouth opening 4 and onto absorbent material 17. When an air-liquid management system, via either of the disclosed embodiments herein, is combined with the particularly proportioned pin height A, pin groove height B, pin diameter C, lower pin head angle D, upper pin head angle E, pin groove width and depth F and groove number, a uniform dispersion rate can be achieved.

For example, there was performed an experiment herein wherein particularly proportioned parameters of pin 15 were tested with a fragrance formulation consisting of water, ethanol, diethylene glycol monobutyl ether, ethoxylated linear alcohol C12-15 with ethylene oxide and fragrance oil. All evaluations used a lower pinhead angle D of 60° and an upper pinhead angle of 30°.

Figure 13:
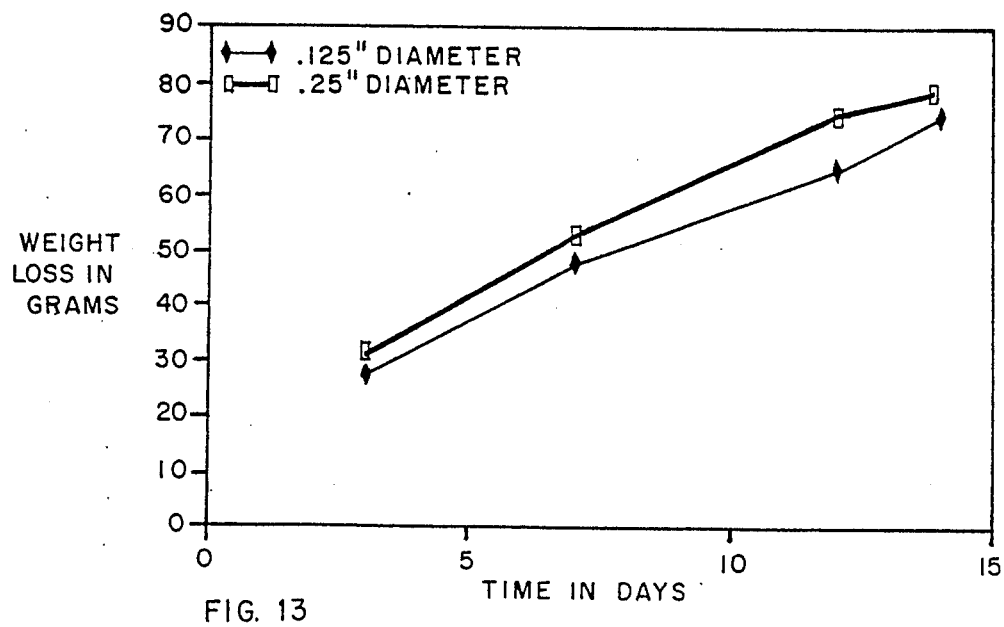
FIGS. 13-16 are graphs plotting the dispersion rates of different pin diameters, heights, groove sizes and groove numbers, respectively.

As shown in FIG. 13, different pin diameter sizes were evaluated for their ability to provide a uniform dispersion rate over a two week period. It was found that both the ¼ inch and ⅛ inch pin diameter worked very well, but the ⅛ inch (0.125 inch) seemed to show a more steady, continuous dispersion.

Figure 14:
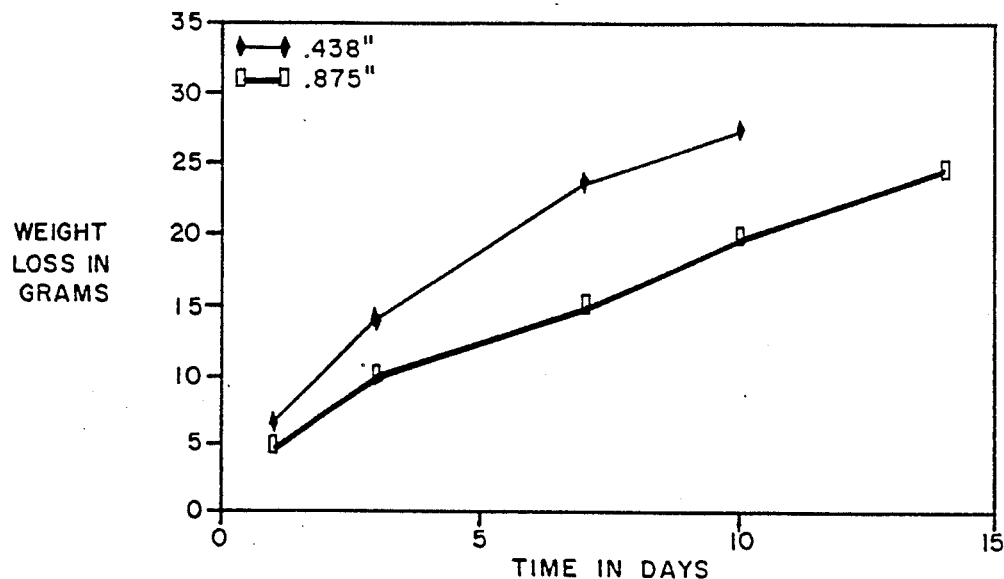

Pin height was then evaluated with a pin of ⅛ inch diameter and groove size of 0.0625 inch × 0.0625 inch (width × depth), as shown in FIG. 14. It was found herein that a pin height of 0.875 inch showed a rather steady, uniform dispersion rate. Pin height is very important, as it is not enough for the pin to merely pierce the mouth opening seal; the pin must clear the meniscus in the well of the mouth opening, otherwise fluid flow will be impeded.

Figure 15:
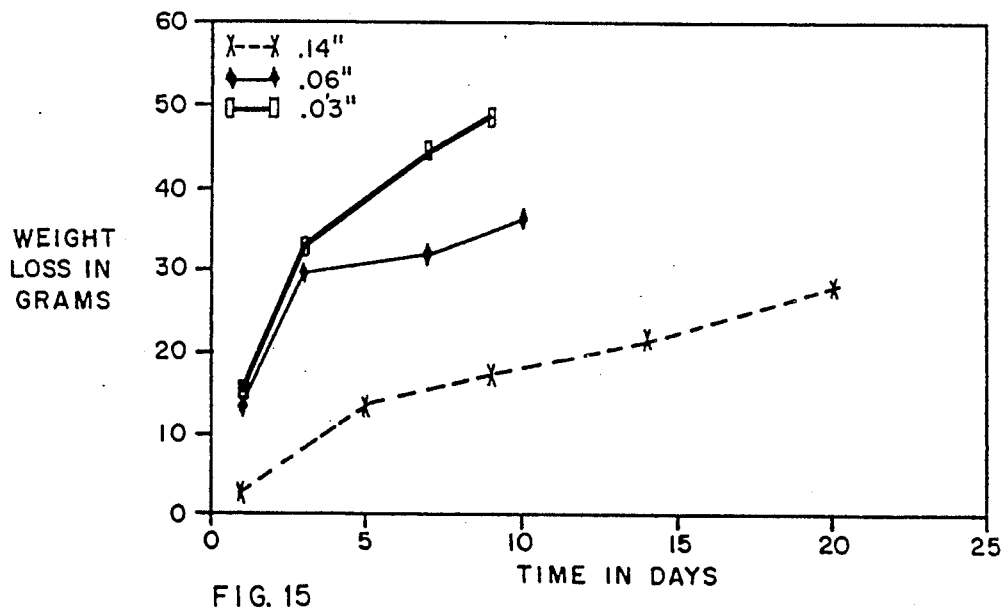

FIG. 15 shows the evaluation of different pin groove sizes (width and depth being equal). A pin groove size of 0.03 inch was found to work most efficiently to provide a uniform dispersion rate.

Figure 16:
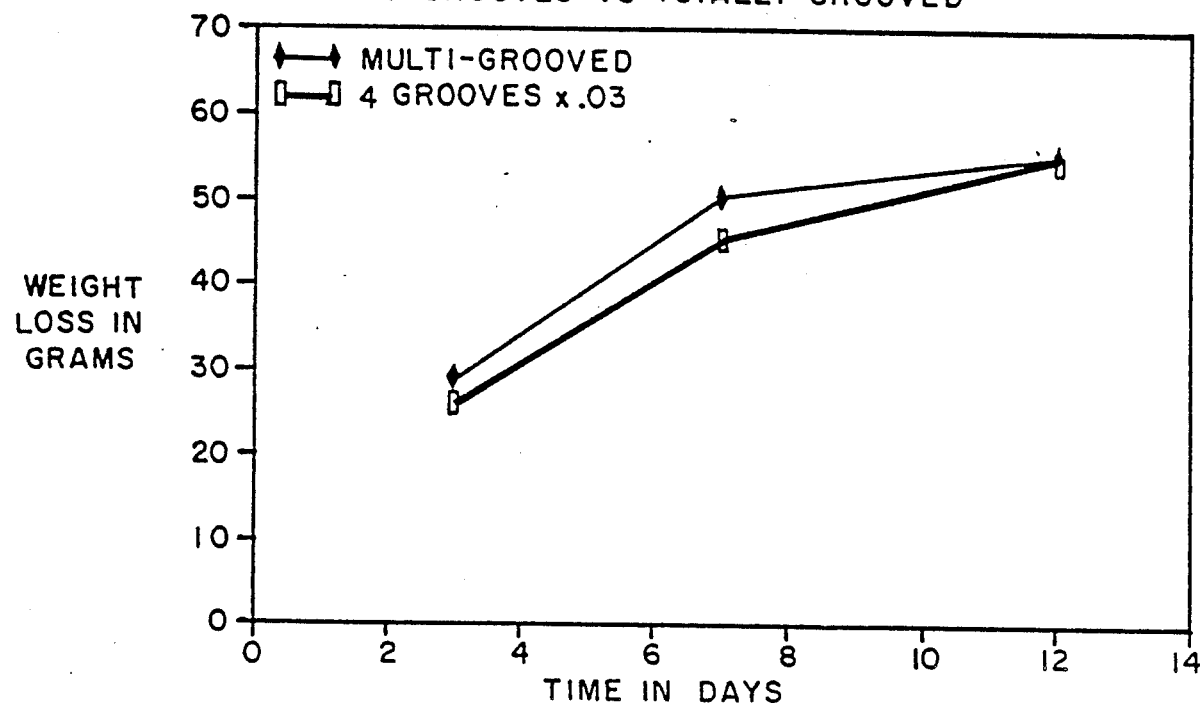

Finally, referring to FIG. 16, a pin of ⅛ inch diameter and 0.03 inch groove size was evaluated with respect to the number of grooves. It was found that a pin with four (4) grooves provided a more uniform dispersion rate than a multi-grooved pin.

Hence, as one example, a pin of 0.875 inch in height with four grooves having 0.03 inch groove size and a diameter of ¼ inch or ⅛ inch will work very well to provide a truly uniform dispersion rate. However, it must be particularly noted that the foregoing is merely a purely illustrative sample of effectively proportioned pin parameters that will provide the desired results and, accordingly, should not be limited to such.

The ability to design into this device a dispersion rate of particular uniformity is a fundamental aspect of the disclosed technology. The regulatory nature of this gravity fed device is achieved through the selection of an air-liquid management system and cellulosic fabric in conjunction with a grooved pin of particular proportions in which the liquid being transported out of the reservoir is made available to the absorption material at a rate influenced by the effectively proportioned grooved pin.

The advantage of a gravity fed device which continuously replenishes the absorption material with fresh volatile components and which, in its fabrication, does not subject the components to harmful processing environments signals an important advantage over other devices designed for air treatment and deodorization. This can be attributed to the fact that the most volatile and fugitive components of the air treatment liquid, which are often those most easily perceived olfactively, are not prematurely lost and, as a result, are available for dispensing throughout the life of the device.

Figure 9:
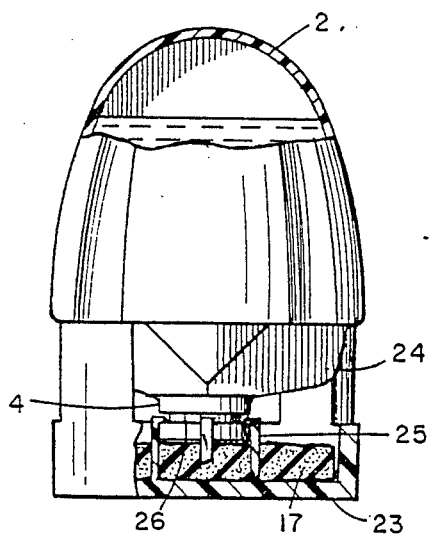
FIG. 9 is a cross-sectional view of a further alternative embodiment of the present invention.
Figure 8:
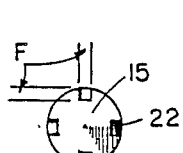
FIG. 8 is a top plan view of that shown in FIG. 7.
Figure 7:
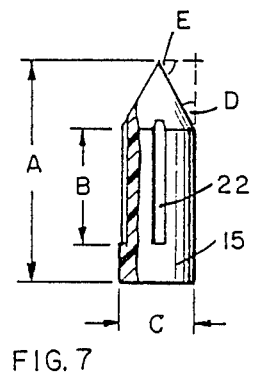
FIG. 7 is a cross-sectional view of the pin of the air treatment device.
Figure 10:
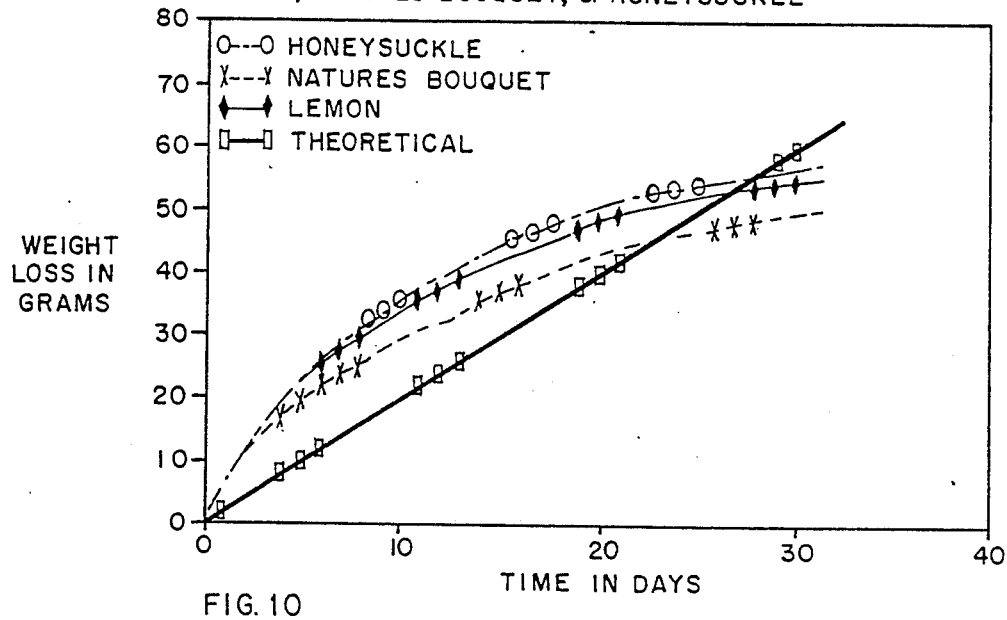
FIGS. 10 and 11 are graphs plotting dispersion rates of various scents of a commercial deodorizer.

FIG. 9 shows a further alternative embodiment of the invention wherein reservoir 2 is locked by different snap-attachment means onto alternatively designed base 23. Base 23 has sidewall segments 24 with apertures therebetween which support reservoir 2 when placed thereon. Extending upwardly from the bottom of base 23 and surrounding the pin are interlocking fingers 25. Mouth opening 4 of reservoir 2 has finger groove 26 circumferentially therearound and in circumferential alignment with the gripping section of interlocking fingers 25 for locking engagement therewith. As is evident from the disclosure herein, the alternative embodiment of FIG. 9 can be employed with control interface 16, or particularly designed so that the effective ebb height distance creates an automatic air-liquid management system, both operating as described herein.

While in the foregoing there is set forth a detailed description of numerous embodiments of the present invention, the embodiments must be considered simply as illustrative. In this regard, the scope of the invention is indicated by the following claims in view of the preceding description, and the claims are intended to embrace all changes that come within their meaning and range of equivalency.

What is claimed is:

1. An air treating device comprising a liquid reservoir having a mouth opening, a base supporting and surrounding a liquid absorbent material, piercing means extending upwardly from said base and absorbent material, means for attaching said reservoir to said base such that said piercing means is in direct alignment with said mouth opening, and liquid metering control means surrounding said piercing means and between said mouth opening and said absorbent material, whereby said device provides a rate of dispersion which is substantially even over an extended period of time, and wherein said liquid metering control means is an effectively distant ebb height between the bottom of said mouth opening and the top surface of said absorbent material, said effective ebb height being adapted to hydraulically cease flow from said reservoir when said absorbent material is saturated and prevent contact between said absorbent material and said mouth opening.

2. The device of claim 1 being of two-piece construction and wherein said mouth opening is sealed until said device is activated.

3. The device of claim 2 further comprising means to adjust the level of emitted air treating liquid.

4. The device of claim 3 wherein said base further comprises a plurality of sidewall segments having apertures therebetween.

5. The device of claim 4 wherein said adjustment means comprises a plurality of longitudinal slots and aperture limiting means around the circumference of said reservoir, said reservoir adapted to be in rotational engagement with said base to selectively place said slots or said aperture limiting means in alignment with said apertures.

6. The device of claim 1 wherein said attachment means comprises a friction fit caused by slidably mounting said reservoir onto said base.

7. The device of claim 1 wherein said attachment means comprises at least one lateral bead around the circumference of said reservoir adapted to correspondingly mate with at least one circumferential groove around the sidewall of said base.

8. The device of claim 7 wherein said mating is caused by snapping or screwing said reservoir onto said base.

9. The device of claim 1 wherein said attachment means comprises interlocking fingers upwardly extending from said base and adapted to engage in locking fashion with a groove located circumferentially around said mouth opening.

10. The device of claim 1 wherein said piercing means is a grooved pin.

11. The device of claim 10 wherein pin height, pin diameter, pin groove size and pin groove number are effectively proportioned to influence the rate of liquid being transported out of said reservoir to said absorption material.

12. An air treating device comprising a liquid reservoir having a mouth opening, a base supporting and surrounding a liquid absorbent material, piercing means extending upwardly from said base and absorbent material, means for attaching said reservoir to said base such that said piercing means is in direct alignment with said mouth opening, and liquid metering control means surrounding said piercing means and between said mouth opening and said absorbent material, whereby said device provides a rate of dispersion which is substantially even over an extended period of time, and wherein said liquid metering control means is an effectively sized mesh-like material.

13. The device of claim 12 further comprising means to adjust the level of emitted air treating liquid.

14. The device of claim 13 wherein said base further comprises a plurality of sidewall segments having apertures therebetween.

15. The device of claim 14 wherein said adjustment means comprises a plurality of longitudinal slots and aperture limiting means around the circumference of said reservoir, said reservoir adapted to be in rotational engagement with said base to selectively place said slots or said aperture limiting means in alignment with said apertures.

16. The device of claim 12 wherein said attaching is caused by snapping or screwing said reservoir onto said base.

17. The device of claim 12 wherein said attachment means comprises interlocking fingers upwardly extending from said base and adapted to engage in locking fashion with a groove located circumferentially around said mouth opening.

18. The device of claim 12 wherein said piercing means is a grooved pin.

19. The device of claim 18 wherein pin height, pin diameter, pin groove size and pin groove number are effectively proportioned to influence the rate of liquid being transported out of said reservoir to said absorption material.

20. A process for treating air comprising attaching a liquid reservoir having a mouth opening onto a base, said base supporting and supporting a liquid absorbent material, aligning a piercing pin extending upwardly from said base with said mouth opening, and controlling liquid metering from said reservoir to said absorbent material to effect a rate of dispersion which is substantially even over an extended period of time, wherein said controlling is performed by an effectively sized mesh-like material surrounding said piercing pin and located between said mouth opening and said absorbent material.

21. A process for treating air comprising attaching a liquid reservoir having a mouth opening onto a base, said base supporting and surrounding a liquid absorbent material, aligning a piercing pin extending upwardly from said base with said mouth opening, and controlling liquid metering from said reservoir to said absorbent material to effect a rate of dispersion which is substantially even over an extended period of time, wherein said controlling is performed by an effectively distant ebb height between the bottom of said mouth opening and the top surface of said absorbent material, said effective ebb height being adapted to hydraulically cease flow from said reservoir when said absorbent material is saturated and prevent contact between said absorbent material and said mouth opening.

* * * * *